United States Patent [19]

Stewart et al.

[11] 4,055,986
[45] Nov. 1, 1977

[54] BASIC SEDIMENT AND WATER MEASUREMENT

[75] Inventors: Thomas L. Stewart; Edward R. Cadena, both of Houston, Tex.

[73] Assignee: Shell Oil Company, Houston, Tex.

[21] Appl. No.: 752,342

[22] Filed: Dec. 20, 1976

[51] Int. Cl.$^2$ ............................................. G01N 15/04
[52] U.S. Cl. ................................. 73/61 R; 73/61.1 R
[58] Field of Search ................. 73/53, 61 R, 61.1 R, 73/61.4, 61.3

[56] References Cited

U.S. PATENT DOCUMENTS

| | | | |
|---|---|---|---|
| 3,003,106 | 10/1961 | Vesper et al. | 73/61 R X |
| 3,005,554 | 10/1961 | Kuntz | 73/61 R X |
| 3,167,949 | 2/1965 | Stenzel et al. | 73/61 R X |
| 3,192,764 | 7/1965 | Jasek | 73/61.1 R |
| 3,222,918 | 12/1965 | Kuntz et al. | 73/53 |
| 3,253,606 | 5/1966 | Kuntz | 73/53 X |
| 3,357,236 | 12/1967 | Kasten | 73/61 R |
| 3,971,248 | 7/1976 | Christensen | 73/61.1 R |

*Primary Examiner*—Jerry W. Myracle
*Assistant Examiner*—Joseph W. Roskos

[57] ABSTRACT

Basic sediment and water content of crude oil flowing through a pipeline is measured by removing a representative sample of the crude oil, heating the sample, and centrifuging the sample to separate the water from the oil. The vapor pressure in the centrifuge is controlled to prevent the escape of any water which has been vaporized by the heating step. The water fraction is passed to a condenser to condense whatever water was vaporized during the heating. Following the condensing step, the water flows into a measuring vessel and is measured.

7 Claims, 1 Drawing Figure

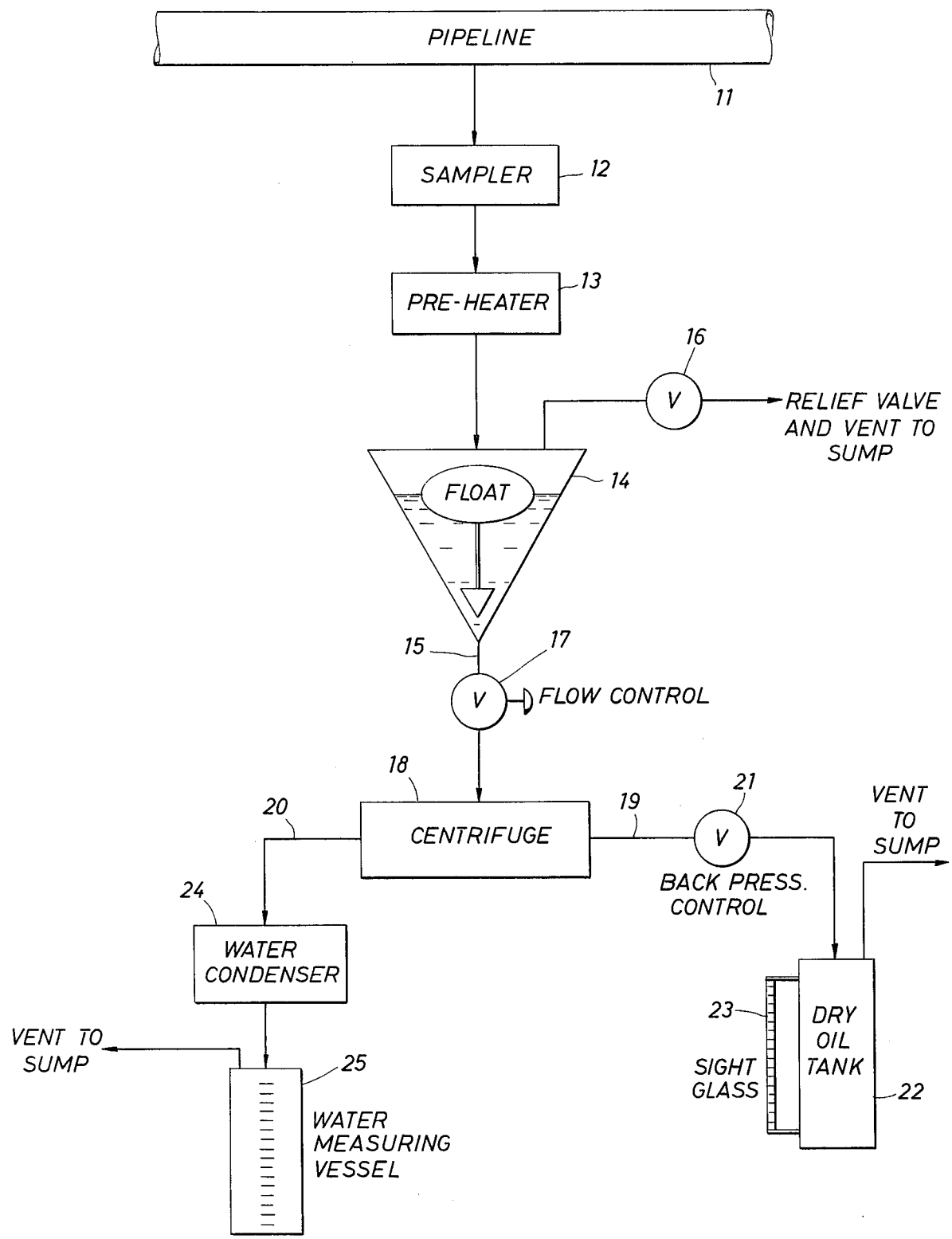

BASIC SEDIMENT AND WATER MEASUREMENT

BACKGROUND OF THE INVENTION

Basic sediment and water (BS&W) constitutes a fraction of one percent of the crude oil transferred into and out of a conventional pipe-line system. Various methods have been developed for measuring the BS&W content of crude oil. For example, samples of the curde can be taken and analyzed for BS&W content. Also, it is possible to use capacitor-type measuring instruments to measure the BS&W content of the crude as it flows through a meter and eliminate the need to take samples. The latter approach is favored, since it permits automatic operation without requiring the attention of outside personnel to obtain representative samples and conduct analysis of the crude. Also, the signal from the BS&W monitor can be used to compensate the flow meter or other measuring instruments to correct for the BS&W content.

The BS&W monitors of the capacitance type, which detect water by means of change in dielectric constant of an oil stream flowing through a conduit, suffer from a number of disadvantages. While the capacitance monitor may be extremely accurate, it is often adversely affected by certain uncommonly existing conditions. For example, the monitor must measure a homogenious mixture in order to achieve a permissible degree of accuracy. Laminar flow in which the oil and liquid tend to separate into different phases is not conducive to efficient monitor operation. Also, slug-type flow in which successive slugs of water and oil flow through the line adversely effects the monitor. A more serious problem arises when the type of crude oil is changed, since this requires a change in the calibrating standard of the BS&W monitor. Since all capacitance-type monitoring equipment measures the dielectric strength of the material disposed between the plates of the measuring cell, any change in the dielectric constant of the crude requires a correponding change in the monitor which cause measurement interruption and gives rise to further chances of error. Of course, even a small error of measuring can result in a substantial financial loss due to the extremely large quantities of oil moving through the pipeline.

SUMMARY OF THE INVENTION

The present invention pertains to a method and apparatus for determining the amount of oil flowing through a pipeline wherein the oil contains a small amount of water and other separable contaminants commonly called BS&W.

The primary purpose of the present invention resides in providing a method and apparatus of high accuracy and reliability, and which is relatively easy of operation for measurement of BS&W content of flowing oil.

In achieving the above purpose, a representative sample of the crude oil is removed from the pipeline, followed by heating the sample and centrifuging it to separate the BS&W from the oil. The vapor pressure in the centrifuge is controlled to permit the escape of any water which has been vaporized by the heating step. The water fraction and vapor are passed to a condenser to condense whatever water is vaporized during the heating. Following the condensing step, the water flows into a measuring vessel and is measured.

DESCRIPTION OF THE DRAWINGS

A schematic BS&W separation system is shown in the drawing.

DESCRIPTION OF PREFERRED EMBODIMENTS

Referring now to the drawings, numeral 11 designates a pipeline through which a crude petroleum containing water and other separable contaminants such as BS&W is flowed. Sampler 12 is employed to remove a portion of oil from the pipeline for measurement purposes. Some samplers encapsulate the sample in the center of the stream and withdraw it from the line. Others use a pitot probe and control velocity in the probe to match that in the stream. Probe diameter in either case must be sufficient to pass easily the largest possible water globule. In the case of the pitot tube, the volume sampled is large and the slip stream generated must be sampled by a total-flow intermittent sampler. With the capsule-type sampler, piping must be arranged to remove the sample positively without any water or sediment. Any of these samplers is suitable for use for the present invention although the capsule type is preferred. Oil is removed by the sampler at a rate of 50 to 100 gph.

The crude oil is heated in preheater 13 above its cloud point before entering a centrifuge. This is to prevent mismeasurement by precipitation of any wax with the sediment and to prevent fouling of the centrifuge with wax accumulation. A holding tank 14 is provided with controlled outflow. This tank accommodates large slugs generated by a full-flow intermittant sampler. Additionally, it assures that liquid, rather than foam or gas, is delivered to the centrifuge. The preheated oil is foamy and the holding tank is sealed to prevent vapor loss. Outlet 15 is float controlled to assure that only liquid goes to the centrifuge and flow controlled by valve 17 to assure a reasonable steady rate within the centrifuge's capability. Pressure relief valve 16 occasionally vents to the sump.

Centrifuge 18 has a rotating element (not shown) which is maintained at a temperature above the crude oil's cloud point. Therefore, the centrifuge is housed such that ambient and internally generated heat will maintain the necessary temperature. Liquid and vapor leave the centrifuge through two lines 19 and 20. Line 19 carries dry oil only, and line 20 carries primarily water and water vapor, together with a small amount of oil vapor. Dry oil in line 19 passes through a back pressure control 21, to a dry oil tank 22, with a graduated sight glass 23 and thermometer (not shown). The dry oil tank holds a relatively large quantity, preferably about 100 gallons, so that the small fraction of BS&W produced will be a readily measurable quantity. The height of the tank is preferably about 8 inches, which allows the oil volume to be measured to about ± 1 part in 1600. The thermometer extends toward the center of the tank to obtain an average temperature for volume correction. The tank is internally coated and has the same ambient temperature as the centrifuge in order to minimize wax deposition and measurement error.

Dry oil is scooped from the rotating mass of fluid in centrifgue 18 by a centripital pump (not shown). A small back pressure is maintained on the dry oil stream exiting the centrifuge by back pressure control 21 in order to contain the oil vapor within the centrifuge.

Water and water vapor in line 20 are passed to a water condenser 24. Inside the centrifuge 18, the separated water exposes a large surface to turbulent, warm air. As a result, much of the water exits the centrifuge as vapor which makes condenser 24 necessary to account for all of the water. Exiting the condenser are liquid water, a trace of liquid oil, and vapors of the light hydrocarbons. The amount of hydrocarbon is negligible for measurement purposes.

All the water is retained and measured in a standard laboratory two-liter, graduated cylinder 25 or any other conventional water-measuring vessel. The vessel is corked or otherwise closed, and the trace amounts of uncondensed hydrocarbon vapors are vented. The oil found on top of the water assures that no water is lost by vaporation. Preferably, graduations are at 20-milliliter intervals, which is less than one part in ten thousand of the total oil and BS&W. It is feasible to measure the water with an accuracy, compared to the total oil, within a range of 0.01% to 0.1%.

EXAMPLES

A 100 gallon tank containing 378,533 milliliters of dry oil is employed. Its diameter is constant over an 80 inch interval of its height and is such that the 80 inch interval corresponds to 378,533 milliliters.

The graduated sight glass of the oil tank is read to the nearest 0.1 inch or ± 0.05 inch. This is ± 1 part in 1600 of the 80 inches.

A corresponding graduated water vessel is read to the nearest 20 milliliters (± 10 ml), which is ± 10/378,533 or ± 0.0026% of the dry oil.

While the present invention has been described with respect to the determination of BS&W in a crude oil stream, it is apparent that it can be used to determine the amount of contaminant material in almost any liquid stream.

We claim as our invention:

1. A process for measuring the water and sediment content of crude oil flowing through a pipeline comprising removing a representative sample of the crude oil from the pipeline, heating the sample, centrifuging the sample to separate the water and sediment from the oil, controlling the vapor pressure in the centrifuge to prevent the escape of any water which has been vaporized by the heating step, passing the water fraction to a condenser to condense whatever water was vaporized during the heating, measuring the water, passing the oil to a tank and measuring the oil.

2. A process of claim 1 wherein a small back pressure is maintained on the dry oil stream exiting from the centrifuge in order to contain oil vapor within the centrifuge.

3. The process of claim 1 wherein the oil is heated above its cloud point.

4. The process of claim 1 wherein the centrifuge has a rotating element which is maintained at a temperature above the oil's cloud point.

5. The process of claim 1 wherein the oil is passed to a holding tank after heating and before being centrifuged and the tank is float-controlled to maintain a liquid level therein which assures that only liquid and not foam resulting from the heating step goes to be centrifuged.

6. The process of claim 1 wherein the tank for measuring oil contains from about 50 to about 200 gallons.

7. The process of claim 1 wherein the water is measurable to ± 10 ml, which is about one part in 18,900 to 75,700 of the total oil and basic sediment and water.

* * * * *